(12) United States Patent
Rao et al.

(10) Patent No.: US 10,588,995 B2
(45) Date of Patent: Mar. 17, 2020

(54) STERILIZATION TRAY FASTENER AND RELATED METHODS

(71) Applicant: Specialty Surgical Instrumentation, Inc., Antioch, TN (US)

(72) Inventors: Sejal Rao, Cliffside Park, NJ (US); Jose Fernandez, Foxborough, MA (US); Drew Jones, Nashville, TN (US); Tom Sullivan, Princeton, NJ (US)

(73) Assignee: Specialty Surgical Instrumentation, Inc., Anitoch, TN (US)

( * ) Notice: Subject to any disclaimer, the term of this patent is extended or adjusted under 35 U.S.C. 154(b) by 0 days.

(21) Appl. No.: 15/606,595

(22) Filed: May 26, 2017

(65) Prior Publication Data

US 2018/0339077 A1   Nov. 29, 2018

(51) Int. Cl.
| | |
|---|---|
| *A61L 2/26* | (2006.01) |
| *B65D 21/032* | (2006.01) |
| *A61B 50/33* | (2016.01) |
| *A61B 50/34* | (2016.01) |
| *A61B 50/00* | (2016.01) |
| *A61B 50/30* | (2016.01) |

(52) U.S. Cl.
CPC .............. *A61L 2/26* (2013.01); *A61B 50/33* (2016.02); *A61B 50/34* (2016.02); *A61B 2050/007* (2016.02); *A61B 2050/0067* (2016.02); *A61B 2050/3007* (2016.02); *A61B 2050/3011* (2016.02); *A61L 2202/121* (2013.01); *A61L 2202/123* (2013.01)

(58) Field of Classification Search
CPC ............ B65D 25/2811; B65D 25/2829; B65D 25/2832; B65D 21/0224; B65D 2501/24649; A45F 5/021; B44D 3/14; A61B 2050/3009; A61B 2050/3007; A61B 2050/0067; A61B 2050/007; A61B 2050/0084; A61L 2202/123; Y10T 24/44026; Y10S 24/91
USPC .................................................. 220/770, 756
See application file for complete search history.

(56) References Cited

U.S. PATENT DOCUMENTS

| | | | |
|---|---|---|---|
| 4,245,807 A * | 1/1981 | York ........................ | A01K 7/00 |
| | | | 248/310 |
| D480,555 S * | 10/2003 | Bledsoe ....................... | D3/215 |
| 6,874,634 B2 | 4/2005 | Riley | |
| 6,962,265 B1 * | 11/2005 | Zhang .................... | A47G 19/22 |
| | | | 220/754 |
| 7,510,096 B2 | 3/2009 | Wang | |
| 7,690,856 B2 | 4/2010 | Mortensen | |
| 7,748,529 B2 | 7/2010 | Foreman et al. | |
| 7,854,340 B1 | 12/2010 | Baker et al. | |
| 7,905,353 B2 | 3/2011 | Baker et al. | |

(Continued)

*Primary Examiner* — Allan D Stevens
(74) *Attorney, Agent, or Firm* — Hayes Soloway P.C.

(57) ABSTRACT

Sterilization tray fasteners are disclosed herein. The disclosed sterilization tray fasteners may be formed to join sterilization tray bases stacked directly on top of one another together. In some embodiments, sterilization tray bases may be formed to have slots or apertures to accommodate features of the disclosed fasteners. For example, in some embodiments, the disclosed sterilization tray fasteners include an elongate body and two curved arms that can extend into apertures of the sterilization tray bases. In many embodiments, the disclosed fasteners can be attached to and detached from sterilization tray bases without tools.

4 Claims, 6 Drawing Sheets

(56) References Cited

U.S. PATENT DOCUMENTS

| | | |
|---|---|---|
| 7,909,191 B2 | 3/2011 | Baker et al. |
| 8,236,253 B2 | 8/2012 | Coyle et al. |
| 8,567,796 B2 | 10/2013 | Bar-Erez et al. |
| 8,733,570 B1 | 5/2014 | Baker et al. |
| 2006/0191939 A1 | 8/2006 | Baker et al. |
| 2008/0000899 A1 | 1/2008 | Baker et al. |
| 2008/0010782 A1* | 1/2008 | Sturdy ............... A45F 5/02 24/3.3 |
| 2008/0190932 A1 | 8/2008 | Orr |
| 2009/0050587 A1 | 2/2009 | Sandor |
| 2011/0114585 A1 | 5/2011 | Abene |
| 2015/0053676 A1 | 2/2015 | Sand |
| 2015/0060503 A1* | 3/2015 | Davis ............... A45F 5/00 224/148.7 |
| 2017/0253379 A1* | 9/2017 | Wangler ............ B65D 25/2829 |

* cited by examiner

STERILIZATION TRAY FASTENER AND RELATED METHODS

FIELD OF THE DISCLOSURE

The present disclosure is generally related to medical instrument sterilization devices and more particularly is related to a fastener for connecting medical instrument sterilization trays and related methods of manufacture and use.

BACKGROUND OF THE DISCLOSURE

Thorough sterilization and proper storage of medical instruments is critical to avoid contamination and resulting issues. Without properly sterilized medical instruments, procedures performed with those instruments are susceptible to causing infection and spreading disease. As such, it is important for medical instruments to be sterilized completely after each time they are used and stored in a way that preserves their sterilized state until use.

Various techniques can be used to achieve sterilization, including subjecting instruments to high pressure and high temperature in an autoclave. Other sterilization techniques employ chemicals, such as ethylene oxide and/or hydrogen peroxide, sometimes using environments of steam, dry heat, with or without irradiation.

SUMMARY OF THE DISCLOSURE

Sterilization trays are commonly used to house dental or surgical instruments during sterilization, including autoclaving and/or other sterilization processes. Various sterilization tray designs are known in the art. For example, some sterilization trays include a base having a rectangular cross-section and a lid shaped to cover the opening of the tray base. In many designs, the sterilization tray base and lid both include apertures to allow fluid to pass through the tray during sterilization. Some sterilization tray designs include a fastener irremovably attached to the tray base that is designed to securely attach the lid (or, in some cases, a different sterilization tray base) to the tray base. However, an irremovable fastener is sometimes undesirable. For example, an irremovable fastener can add additional excess weight, thereby restricting the total weight of the tools and instruments to be placed in the sterilization container.

In some cases, irremovable fasteners may also undesirably add length and/or width to the sterilization tray. Moreover, many irremovable fasteners known in the art are shaped to accommodate sterilization tray lids and do not allow multiple sterilization tray bases to be stacked on top of one another without a lid separating the tray bases.

Instruments needing sterilization are typically placed in a sterilization tray after use, sterilized while retained in the tray, and the instruments remain stored in the tray until they are needed for use. In many circumstances, it could be advantageous to fasten or otherwise group select sterilization trays together. For example, in situations where particular tools or devices are needed for a procedure, a device to fasten trays housing the necessary tools/devices could be used. Additionally, a fastening device that allows sterilization tray bases to be stacked directly on top of one another (without needing a lid for each tray base) could reduce overall weight, thereby allowing more instruments to be sterilized during a single sterilization process.

A sterilization tray fastener is disclosed herein. The disclosed sterilization tray fasteners may be formed to join sterilization tray bases stacked directly on top of one another together. In some embodiments, sterilization tray bases may be formed to have slots or apertures to accommodate the disclosed fasteners. For example, in some embodiments, a first sterilization tray base having four sides and a bottom may have two slots on opposing sides. In some such example embodiments, a second sterilization tray also having two slots may be positioned on top of the first sterilization tray, with the slots of the first sterilization tray directly below the slots of the second sterilization tray. A fastening device as disclosed herein may then be used to join the first and second sterilization trays together. In some example embodiments, the fastening device may be positioned in place by first inserting an arm of the fastener into one of the slots (for example, a slot of the first sterilization tray) and then snapping the second arm of the fastener into the other slot (in this example, the slot of the second sterilization tray).

In some embodiments, the disclosed sterilization tray fastener includes a first arm and a second arm attached to opposing ends of an elongate body. In these and other embodiments, the first arm may extend from a first side of the elongate body and curve back toward to the elongate body such that a surface of the first arm is approximately parallel to the elongate body. In these and other embodiments, the second arm may also extend from the first side of the elongate body and may include a proximal portion that curves to provide a surface approximately perpendicular to the elongate body and a distal portion that curves away from the first arm. In some embodiments, the elongate body, the first arm, and the second arm may be formed as a unitary component and, in select embodiments, may be formed of stainless steel. The elongate body may have a width that is less than a width of the first arm and the second arm, in some instances and in select embodiments, the elongate body, the first arm, and the second arm may each have a thickness that is approximately equal.

BRIEF DESCRIPTION OF THE DRAWINGS

FIGS. 1A and 1B illustrate an exemplary sterilization tray fastener, in accordance with an embodiment of the subject disclosure. Specifically.

FIGS. 2A-2C illustrate an exemplary sterilization tray fastener engaging with two sterilization tray bases. In particular, FIGS. 2A and 2B show a sectional plane view taken along line 2A, 2B of FIG. 3 and FIG. 2C shows a sectional plane view taken along line 2C of FIG. 3.

As will be appreciated, the figures are not necessarily drawn to scale or intended to limit the disclosure to the specific configurations shown. For instance, while some figures generally indicate straight lines, right angles, and smooth surfaces, an actual implementation of the disclosed devices may have less than perfect straight lines, right angles, and smooth surfaces. In other words, the figures are provided merely to show some possible example structures.

Additionally, for purposes of clarity, not every component may be labelled in every figure.

DETAILED DESCRIPTION

Sterilization tray fasteners and methods of manufacturing such fasteners are disclosed herein. In particular, various sterilization tray fastening systems are disclosed having at least two stackable sterilization tray bases and one or more fasteners that are easily attachable to and removeable from the sterilization tray bases. In some embodiments, the sterilization tray bases each include an opening to accommodate a feature of the fastener. For example, in some example embodiments, the fastener includes a body with two arms extending from opposing ends of the body and each arm is shaped to fit inside an opening of a sterilization tray base. In select embodiments, each sterilization tray base includes two opening on opposing sides of the tray base. In these and other embodiments, one or more sterilization tray bases can be stacked such that the openings are aligned over one another and fasteners can be used to connect the tray bases together by inserting the arms of the fasteners into the tray base openings. Unlike other sterilization tray fastening devices, the disclosed sterilization tray base fasteners are easily attachable to and removable from sterilization tray bases without tools, thereby allowing for quick and simple assembly and disassembly.

Example Structures and Methods of Operation

Figure 1A:
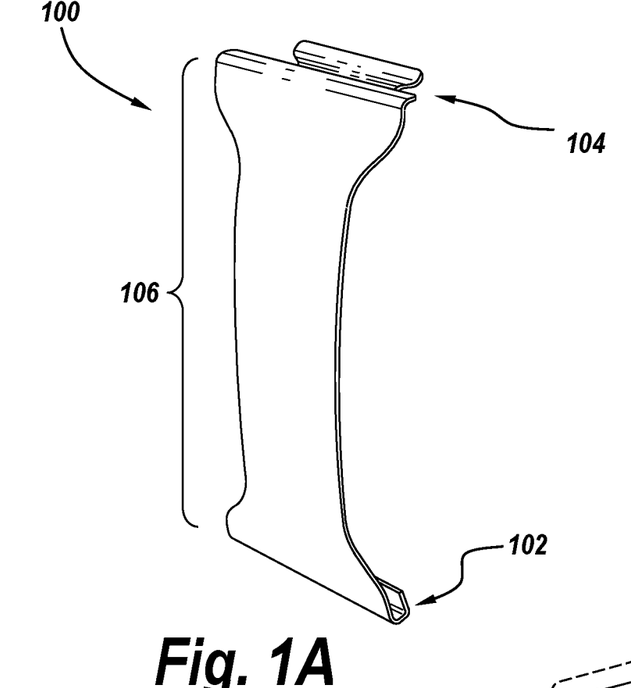
FIG. 1A illustrates a perspective front side view of the exemplary sterilization tray fastener and FIG. 1B illustrates a perspective rear side view of the exemplary sterilization tray fastener.
Figure 1B:
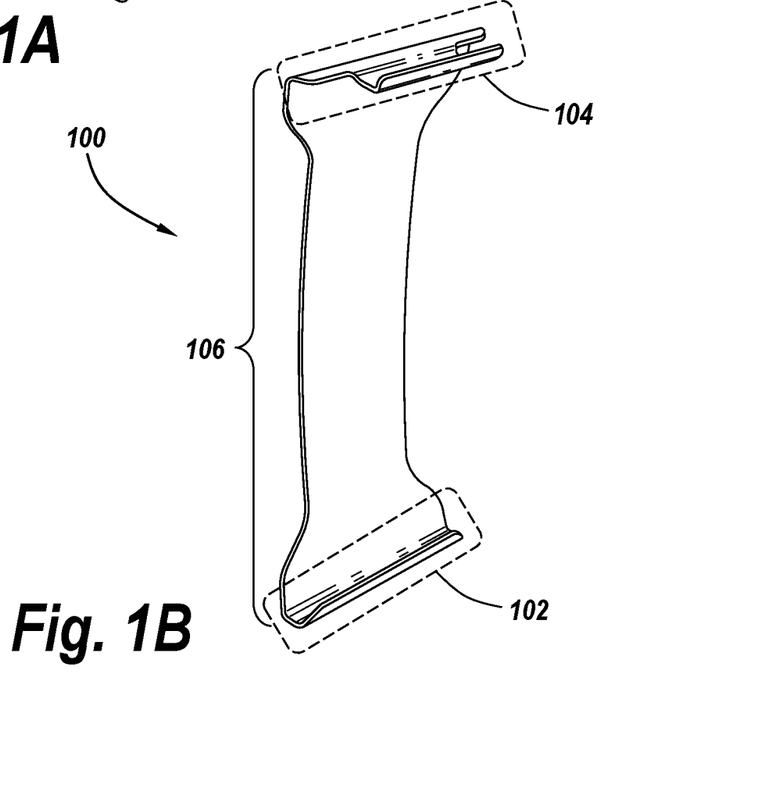

FIGS. 1A and 1B illustrate perspective views of an exemplary sterilization tray fastener, in accordance with one embodiment of the present disclosure. In particular, FIG. 1A illustrates a perspective front side view of the exemplary sterilization tray fastener and FIG. 1B illustrates a perspective rear side view of the exemplary sterilization tray fastener shown in FIG. 1A. As shown in FIGS. 1A and 1B, sterilization tray fastener 100 (at times referred to as simply "fastener" or "fastening device" throughout the subject disclosure) includes an elongate body 106 having an upper end and a lower end, a first arm 102 extending from the lower end, and a second arm 104 extending from the upper end. Sterilization tray fastener 100 may, in some embodiments, be formed of a monolithic material (as shown in FIGS. 1A and 1B), resulting in a unitary component, or, in other embodiments, sterilization tray fastener 100 may be formed of at least two, at least three, or at least four separate, discrete components joined together by any appropriate technique (e.g., by welding or with adhesive). Sterilization tray fastener 100 may be formed of any suitable material, including any material capable of maintaining structural integrity during sterilization, such as metal (for example, stainless steel), or a polymeric material (for example, polypropylene, polyethylene, or polyphenylsulfone).

Figure 2A:
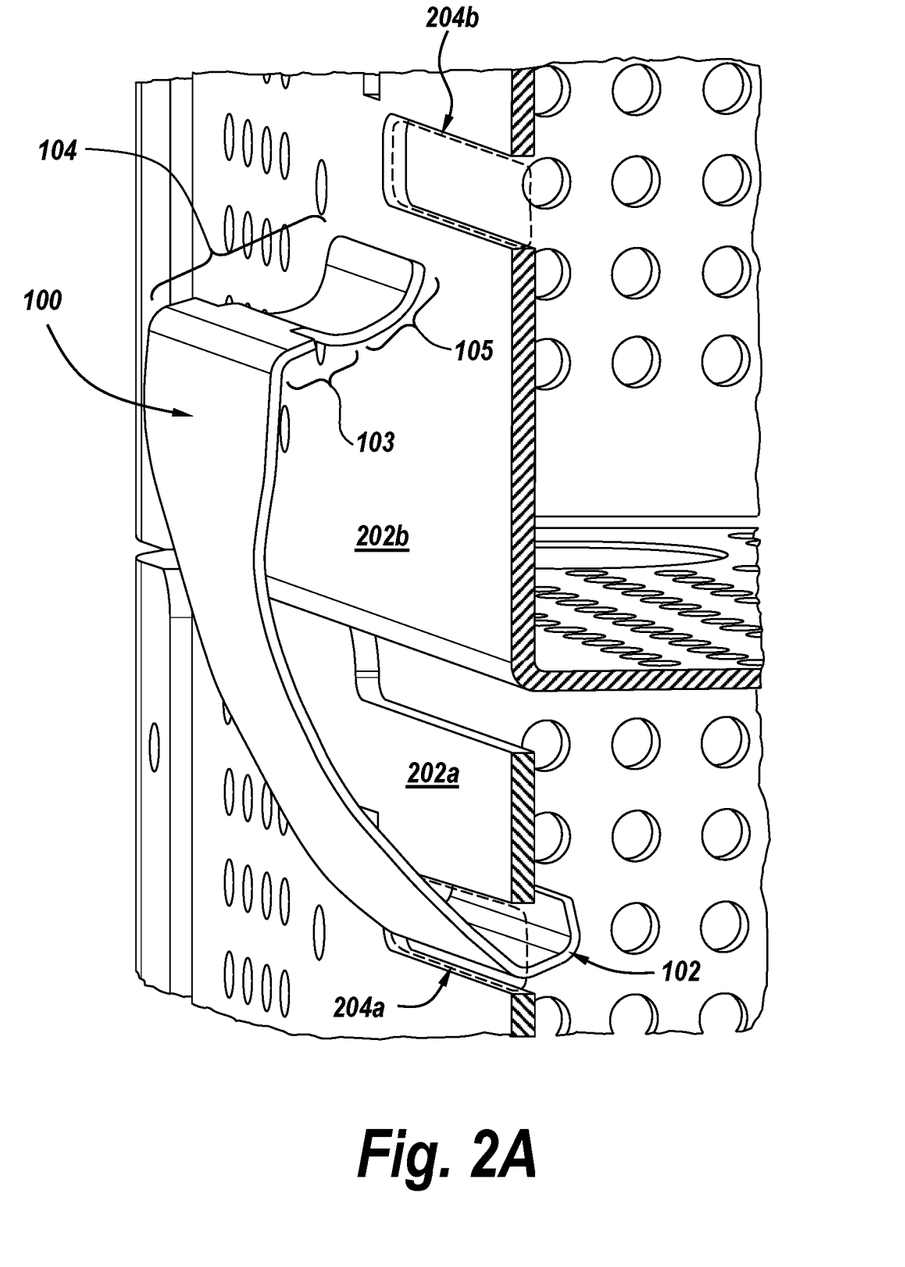
FIGS. 2A and 2B illustrate the exemplary sterilization tray fastener being inserted into openings of two sterilization tray bases and FIG. 2C illustrates the exemplary sterilization tray fastener fully inserted into the sterilization tray base openings, in a locked position.
Figure 2B:
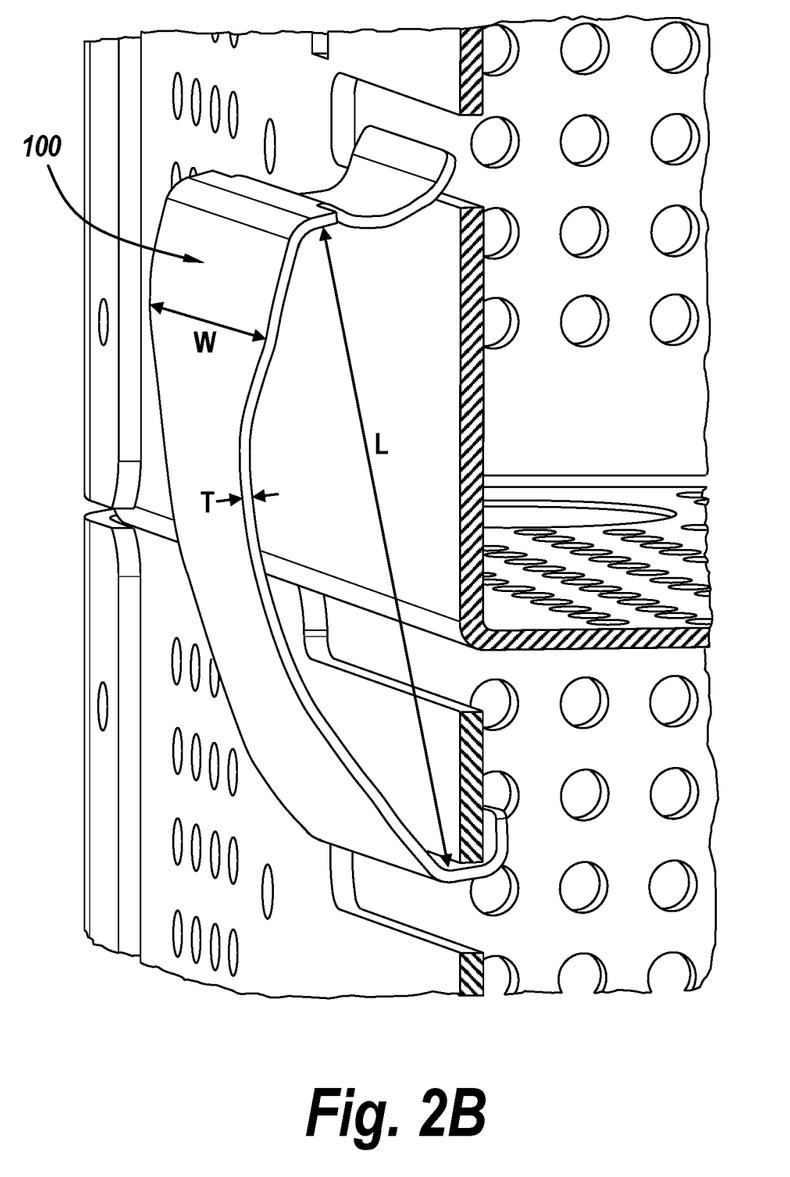
Figure 2C:
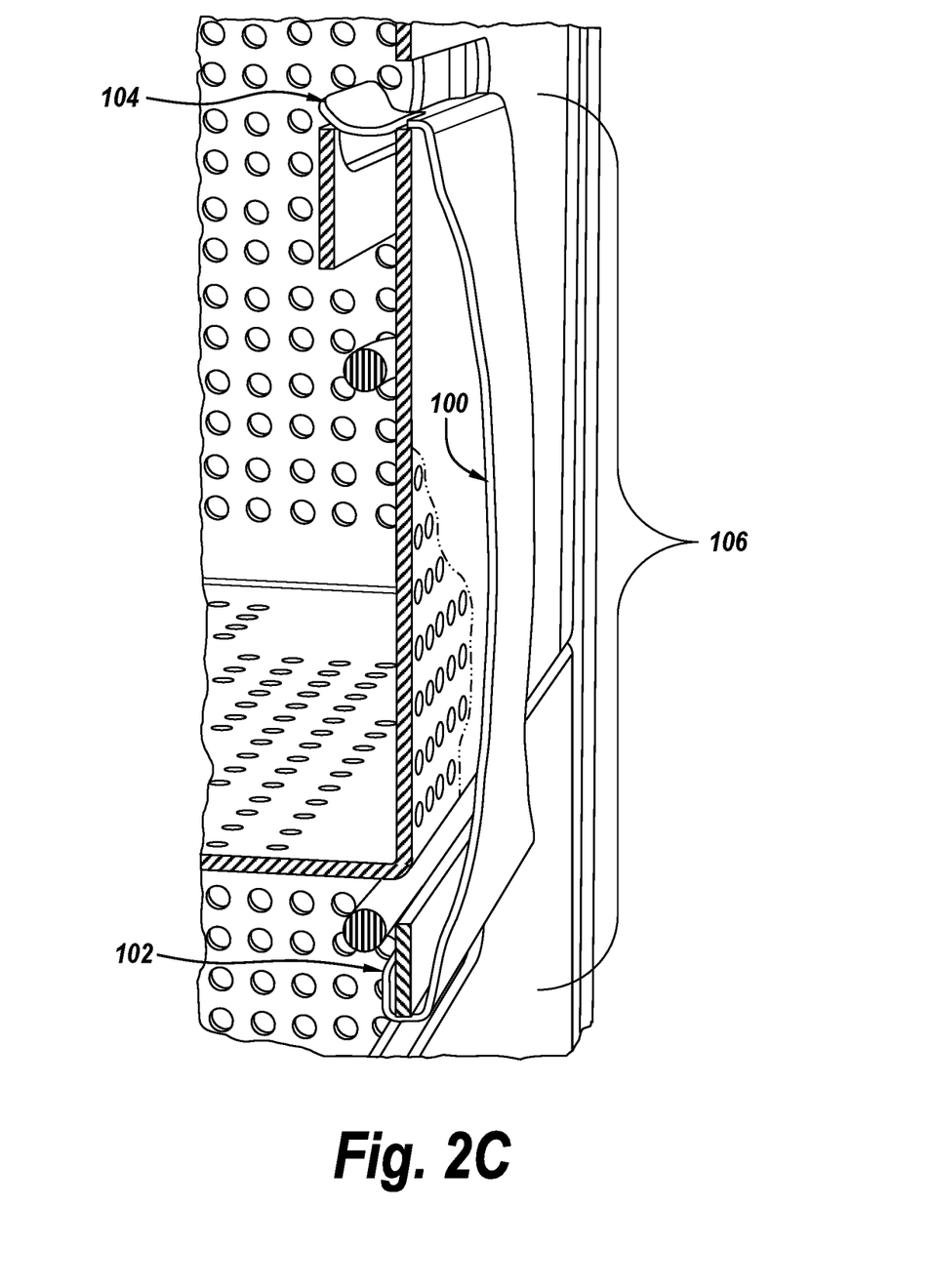

Arms 102 and 104 of sterilization tray fastener 100 may be formed to engage with openings (or slots) of a sterilization tray base 202a, 202b, as illustrated in FIGS. 2A-2C. In particular, arm 102 may be shaped to engage with opening 204a of a first sterilization tray base 202a and arm 104 may be shaped to engage with opening 204b of a second sterilization tray base 202b. For simplicity and ease of understanding, a sterilization tray base (e.g., 202a or 202b) may be referenced, generally, as 'sterilization tray base' or as 'tray base' throughout the subject disclosure. Similarly, an opening in a tray base (e.g., opening 204a or 204b) may be referenced, generally, as 'opening.' Arm 102 and arm 104 may be formed in any suitable shape to permit engagement with an opening of a sterilization tray base. For example, in some embodiments, first arm 102 and second arm 104 may have the same shape, while in other embodiments first arm 102 and second arm 104 may be shaped differently. In some particular embodiments, first arm 102 and second arm 104 may be mirror images of one another. As shown in FIG. 2A, first arm 102 may extend from a side of elongate body 106 and may curve back towards the elongate body 106 such that a surface of first arm 102 is approximately parallel to elongate body 106. The surface of first arm 102 that is approximately parallel to elongate body 106 may be shorter than opening 204a to facilitate insertion into opening 204a. In some embodiments, a cross-section of first arm 102 and elongate body 106 may be substantially u-shaped, as shown in FIGS. 1A and 1B.

In some embodiments, second arm 104 may include a proximal portion 103 and a distal portion 105, as illustrated in FIG. 2A. In accordance with some example embodiments, second arm 104 includes a proximal portion 103 that extends on the same side (i.e., a first side) of elongate body 106 as first arm 102. In these and other embodiments, the proximal portion 103 of second arm 104 may curve to provide a surface that is approximately perpendicular to elongate body 106, as shown in FIG. 2A. In some embodiments, the distal portion 105 of second arm 104 may be curved or straight. For example, in some embodiments where the distal portion 105 of second arm 104 is curved, the distal portion 105 may either curve in towards first arm 102 or may curve away from first arm 102. FIG. 2A illustrates an example fastener having a second arm with a distal portion 105 curving away from first arm 102.

As illustrated in FIGS. 2A and 2B, the ends of both first arm 102 and second arm 104 face upward when positioned in openings 204a and 204b, respectively. In example embodiments where arm 102 and 104 are shaped differently, fastener 100 can include markings to differentiate between arm 102 and arm 104. For example, in some embodiments fastener 100 can include markings to indicate a preferred orientation of fastener 100 with respect to sterilization tray bases 202a, 202b. In some example embodiments, fastener 100 may include markings to indicate the arm of the fastener 100 that should be positioned upward when used in connection with sterilization tray bases 202a, 202b.

Elongate body 106 may be substantially linear between first arm 102 and second arm 104, or, in other embodiments, may be non-linear. For example, the exemplary sterilization tray fastener 100 shown in FIGS. 1A and 1B includes an elongate body 106 that is bow-shaped, having an outer surface that curves away from first arm 102 and second arm 104. In some embodiments, a bow-shaped elongate body 106 may facilitate movement of arms 102 and 104, providing the ability for the sterilization tray fastener 100 to flex.

Sterilization tray fastener can be formed to be attachable to and removable from sterilization tray bases without tools. For example, FIGS. 2A-2C illustrate that fastener 100 can be used to join sterilization tray 202a to sterilization tray 202b by simply inserting first arm 102 into opening 204a of tray base 202a and then snapping second arm 104 into opening 204b of tray base 202b. Fastener 100 can similarly be removed from tray bases 202a, 202b by pulling second arm 104 from opening 204b (either by pulling fastener body 106 from the outside of tray base 202b and/or by pushing on second arm 104 from the inside of tray base 202b) and subsequently rotating first arm 102 and removing it from opening 204a of tray base 202a. In these and other embodiments, the sterilization tray fastener 100 can be both joined to tray bases and removed from tray bases without using any tools or instruments (other than human hands).

Sterilization tray fastener 100 may have any desired dimensions that permit engagement with the openings of coordinating tray bases. For example, sterilization tray fastener 100 may have a length (L), width (W), and thickness (T) as illustrated in FIG. 2B. As shown in FIGS. 1A and 1B, the sterilization tray fastener 100 may be planar across its width (W) along its entire length (L). In some embodiments, length (L) of fastener 100 may be approximately the distance between openings 204a, 204b of stacked sterilization tray bases 202a, 202b. For example, in some embodiments, fastener 100 may have a length (L) of between 0.5 inches and 6 inches. In some embodiments, fastener 100 has a length of less than 6 inches, less than 5 inches, less than 4 inches, less than 3 inches, or less than 2 inches. In these and other embodiments, fastener 100 may have a length of at least 0.5 inches, at least 1 inch, or at least 2 inches. In some particular embodiments, length (L) of fastener is approximately 1 inch, 1.7 inches, 2 inches, 2.7 inches, 3 inches, 3.7 inches, or 4 inches. Fastener 100 may have a width (W) that is constant along its length or variable along its length (as shown in FIG. 2B. In some example embodiments, fastener 100 may have a width (W) of less than 2 inches, less than 1.5 inches, or less than 1.0 inches at all points. In these and other embodiments, fastener 100 may have a width (W) of greater than 0.5 inches, 1.0 inch, or 1.5 inches at all points. In some particular embodiments, fastener 100 may have a width (W) that varies along its length (L) from approximately 1 inch to approximately 1.7 inches. In some embodiments, the width of the first arm and the second arm of the fastener may be greater than the width of the elongate body. In some such embodiments, fastener 100 may have an overall hourglass shape, as shown in FIGS. 1A and 1B. Fastener 100 may have a uniform thickness (T), in some embodiments, while in other embodiments, thickness (T) of fastener 100 may vary. In some embodiments, thickness (T) of fastener 100 may be less than 0.25 inches, 0.1 inches, or 0.05 inches at some or all points. In these and other embodiments, thickness (T) of fastener 100 may be at least 0.01 inches, 0.05 inches, or 0.1 inches at some or all points. In these or other embodiments, thickness (T) of fastener 100 may be approximately 0.01 inches, 0.02 inches, 0.03 inches, or 0.035 inches. Fastener 100 may be at least partially flexible, permitting at least minimal movement of second arm 104 relative to first arm 102. For example, in some embodiments, fastener 100 may be clipped into place by inserting first arm 102 into an opening 204a of a first sterilization tray base 202a and then inserting second arm 104 into an opening 204b of a second sterilization tray base 202b.

The disclosed sterilization tray fasteners 100 can be produced by any suitable method. For example, in some cases where fastener 100 is formed of a metal (e.g., stainless steel), a sheet of metal can be cut to have the desired dimensions of the fastener. The cut sheet metal can then be bent, crimped, or otherwise formed to have the appropriate curvature. Any suitable technique can be used to shape fastener 100, including but not limited to forcing the metal into a mold having the desired curvature. In some embodiments, heat may be used to facilitate the metal forming process. In embodiments where fastener 100 is formed of a polymer material, any known production technique can be used to form fastener 100. For example, fastener 100 can be injection molded, in some embodiments. Numerous techniques to form fastener 100 will be apparent to one of skill in the art upon consideration of the subject disclosure.

Sterilization tray bases may be formed to have one or more openings to accommodate arms 102 and 104 of fastener 100. In some example embodiments, openings 204a, 204b may be rounded rectangular slots. However, in other embodiments, openings 204a, 204b may take another shape, such as rectangular, oval, rounded, square, or another appropriate shape. A sterilization tray may include more than one opening, in some embodiments. For example, in some embodiments, a sterilization tray base 202a may include two openings positioned on opposing sidewalls. In possible other embodiments, a sterilization tray may include three openings or four openings, all on separate sidewalls. In some embodiments, more than one opening may be included on a single sidewall of a sterilization tray base 202a. In embodiments where a sterilization tray base includes more than one opening, the openings may be positioned equidistantly from the top edge of the sidewalls.

Figure 3:
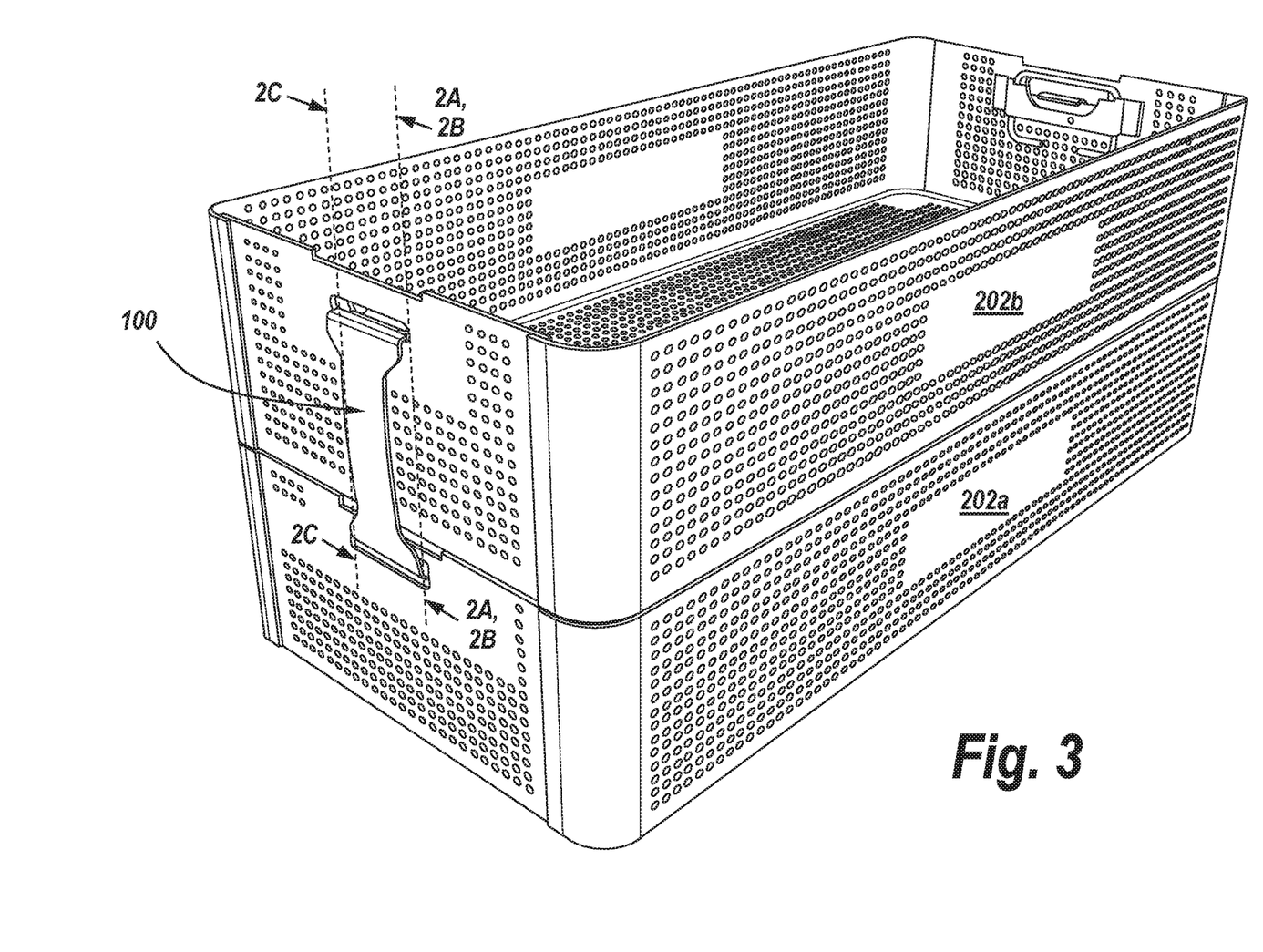
FIG. 3 is a perspective view of an exemplary sterilization tray fastener connecting two sterilization tray bases.

FIG. 3 is a perspective view of two sterilization tray bases attached with fastener 100. While sterilization tray bases 202a and 202b shown in FIG. 3 are of approximately equal size, in some embodiments, a fastener 100 may be used to join sterilization tray bases having different dimensions (e.g., different heights and/or widths). In some embodiments, sterilization tray bases 202a, 202b can be formed to fit on top of one another without the bases receding into one another more than a desired amount. As illustrated in FIG. 3, where sterilization trays are stacked using fastener 100, the bottom of the top sterilization tray base (202b in FIG. 3) can serve as a divider between the sterilization trays, removing the need for the bottom sterilization tray base (202a in FIG. 3) to include a lid and thereby reducing the total weight of the sterilization system. As sterilization cycles typically have a maximum weight limit, reducing excess weight of the sterilization trays and fasteners is highly advantageous.

Figure 4:
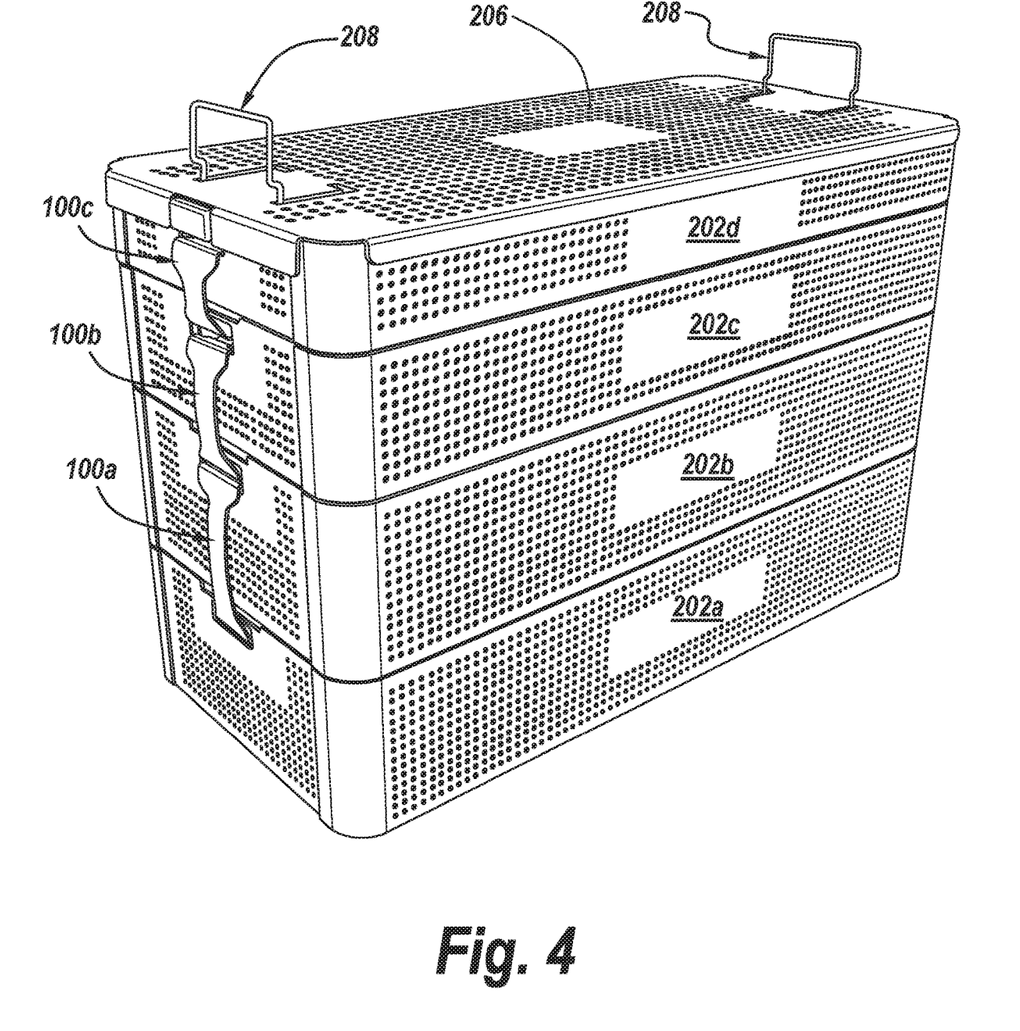
FIG. 4 is a perspective view of three sterilization tray fasteners connecting four sterilization tray bases.

FIG. 4 illustrates multiple sterilization tray bases stacked together and fastened with exemplary sterilization tray fasteners, as disclosed herein. In particular, FIG. 4 illustrates sterilization tray bases 202a-d stacked and fastened with fasteners 100a-c. As shown in FIG. 4, sterilization tray fasteners 100 can have different dimensions, depending on the dimensions of the sterilization trays to be joined, specifically, the upper sterilization tray. For example, sterilization tray 202b has higher sidewalls than tray bases 202c and 202d, and fastener 100a accordingly has a longer length to join tray bases 202a and 202b. Similarly, fastener 100b has a slightly longer length than fastener 100a as it joins sterilization tray base 202b and 202c, which have higher sidewalls than tray base 202d.

In some example embodiments, the disclosed sterilization tray systems include a lid 206, as shown in FIG. 4. Lid 206 may be formed to cover an uppermost sterilization tray base (tray base 202d in FIG. 4). Lid 206 may be fastened to the desired sterilization tray base using any appropriate method. For example, in some embodiments, lid 206 includes a feature that engages with a slot of the tray base 202d. In other embodiments, lid 206 includes a feature that engages with a part of the tray base 202d other than a slot or the tray base 202d includes a feature that engages with the lid 206. In some embodiments, lid 206 includes one or more handles 208, as shown in FIG. 4. The fasteners 100a-c allow all four tray bases 202a-d to be carried by holding the handles 208 attached to the lid 206. FIG. 4 also illustrates that, in some embodiments, two fasteners 100a, 100b or 100b, 100c may share the same slot in a sterilization tray base 202b or 202c. Numerous configurations and variations will be apparent in light of this disclosure.

The features and advantages described herein are not all-inclusive and, in particular, many additional features and advantages will be apparent to one of ordinary skill in the art in view of the drawings, specification, and claims. Moreover, it should be noted that the language used in the specification has been selected principally for readability and instructional purposes, and not to limit the scope of the inventive subject matter described herein. The foregoing description of the embodiments of the disclosure has been presented for the purpose of illustration; it is not intended to be exhaustive or to limit the claims to the precise forms disclosed. Persons skilled in the relevant art can appreciate that many modifications and variations are possible in light of the above disclosure.

What is claimed is:

1. A sterilization tray fastener comprising:
   an elongate body having an upper end and an opposing lower end;
   a first arm extending from the lower end on a first side of the elongate body, the first arm curving back toward to the elongate body such that a surface of the first arm is parallel to the elongate body; and
   a second arm extending from the upper end on the first side of the elongate body, the second arm having a proximal portion and a distal portion, the proximal portion curving to provide a surface perpendicular to the elongate body and the distal portion curving away from the first arm, wherein the sterilization tray fastener has a length extending between the first arm and the second arm and a width and the sterilization tray fastener is planar across its width along the entire length of the fastener, and wherein the elongate body has a width that is less than a width of the first arm and the second arm and the elongate body is bow-shaped with an outer surface that curves away from the first arm and the second arm.

2. The sterilization tray fastener of claim 1, wherein the elongate body, the first arm, and the second arm are formed as a unitary component.

3. The sterilization tray fastener of claim 2, wherein the sterilization tray fastener is formed of stainless steel.

4. The sterilization tray fastener of claim 1, wherein the sterilization tray fastener has an overall hourglass shape.

* * * * *